United States Patent
Shukla et al.

(10) Patent No.: US 7,985,859 B2
(45) Date of Patent: Jul. 26, 2011

(54) PROCESSES FOR THE PREPARATION OF CLOPIDOGREL

(75) Inventors: Jagdish Shukla, Aurangabad (IN); Anjum Reyaz Khan, Aurangabad (IN); Arvind Merwade, Betgeri (IN); Mohammad Jaweed Mukarram Siddiqui, Aurangabad (IN); Yatendra Kumar, Aurangabad (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 0 days.

(21) Appl. No.: 12/601,589

(22) PCT Filed: May 29, 2008

(86) PCT No.: PCT/IB2008/052098
§ 371 (c)(1),
(2), (4) Date: Jan. 30, 2010

(87) PCT Pub. No.: WO2008/146249
PCT Pub. Date: Dec. 4, 2008

(65) Prior Publication Data
US 2010/0130541 A1 May 27, 2010

(30) Foreign Application Priority Data
May 30, 2007 (IN) .................. 1005/MUM/2007

(51) Int. Cl.
*C07D 513/02* (2006.01)
*A61K 31/44* (2006.01)
(52) U.S. Cl. ...................... 546/114; 514/301
(58) Field of Classification Search ............ 546/114
See application file for complete search history.

(56) References Cited

U.S. PATENT DOCUMENTS

| 4,529,596 | A | 7/1985 | Aubert et al. | |
| 7,291,735 | B2 * | 11/2007 | Mukarram et al. | 546/114 |
| 7,446,200 | B2 * | 11/2008 | Deshpande et al. | 546/114 |
| 2005/0113406 | A1 * | 5/2005 | Nagy et al. | 514/301 |
| 2006/0183907 | A1 * | 8/2006 | Mukarram et al. | 546/114 |

FOREIGN PATENT DOCUMENTS

| WO | WO02059128 A2 | 8/2002 |
| WO | WO2004/013147 A1 | 2/2004 |
| WO | WO2005/012300 A1 | 2/2005 |
| WO | WO2006/087729 A1 | 8/2006 |
| WO | WO2006091847 A2 | 8/2006 |
| WO | WO2006/094468 A | 9/2006 |
| WO | WO2006/130852 A1 | 12/2006 |
| WO | WO2008068569 A | 6/2008 |

OTHER PUBLICATIONS

Fox, Marye Anne and Whitesell, James, Organic Chemistry, 1994, Jones and Bartlett, 2nd ed., p. 1, 262.*
Fujima, Y et al. Org. Process Res. & Dev. 2006, 10, 905-913.*
Kozma, David, CRC Handbook of Optical Resolutions via Diastereomeric Salt Formation, 2002, CRC Press, pp. 1-90.*
Renou et al., Synthesis and X-ray structural studies of the dextrorotatory enantiomer of methyl a-5(4,5,6,7-tetrahydro(3,2-c)thieno pyridyl) (2-chlorophenyl)-acetate isopropylsulfate. Journal of Molecular Structure.vol. 827, Issues 1-3, Feb. 17, 2007, pp. 108-113.
Database Sigma Aldrich MSDS. Sigma Aldrich; Product No. 156667. Mar. 6, 2006. "Potassium Ter-Butoxide, Reagent Grade, 95%" XP007905940.

* cited by examiner

*Primary Examiner* — Janet Andres
*Assistant Examiner* — Heidi Reese
(74) *Attorney, Agent, or Firm* — Bio Intellectual Property Services LLC; O. (Sam) Zaghmout

(57) ABSTRACT

The invention relates to processes for the preparation of clopidogrel and salts thereof. The inventors have developed a process for preparing racemic clopidogrel by racemizing R(−) clopidogrel. The process includes the step of reacting R(−) clopidogrel with a powered anhydrous base in one or more solvents.

10 Claims, No Drawings

PROCESSES FOR THE PREPARATION OF CLOPIDOGREL

FIELD OF THE INVENTION

The invention relates to processes for the preparation of clopidogrel and salts thereof. More particularly, it relates to a process for racemizing R (−) enantiomer of clopidogrel.

BACKGROUND OF THE INVENTION

Clopidogrel is an inhibitor of ADP-induced platelet aggregation acting by direct inhibition of adenosine diphosphate (ADP) binding to its receptor and of the subsequent ADP-mediated activation of the glycoprotein GPIIb/IIIa complex.

Clopidogrel bisulfate of formula I, is chemically known as, methyl (+)-(S)-α(2-chlorophenyl)-6,7-dihydrothieno[3,2-c]pyridine-5(4H)-acetate sulfate (1:1).

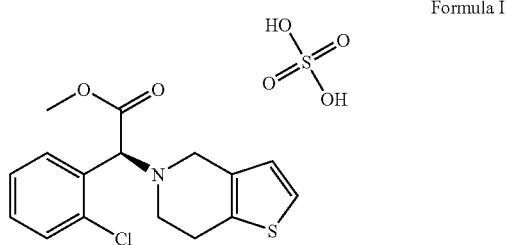

Formula I

Clopidogrel hydrochloride of formula II is chemically known as, methyl (+)-(S)-α-(2-chlorophenyl)-6,7-dihydrothieno[3,2-c]pyridine-5(4H)-acetate hydrochloride. Clopidogrel and its salts are used in the treatment of platelet aggregation inhibitory and anti-thrombotic effect.

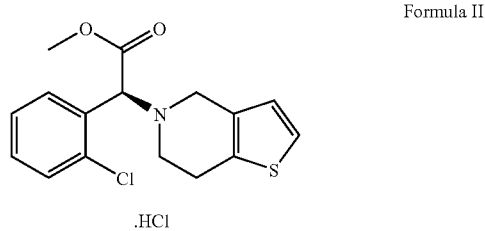

Formula II

U.S. Pat. No. 4,529,596 discloses a racemic mixture of clopidogrel and processes for its preparation. U.S. Pat. No. 5,036,156 discloses a process for preparing an intermediate, 2-chloro-α-bromophenylacetic acid, which is useful in the synthesis of clopidogrel.

U.S. Pat. Nos. 4,847,265; 5,132,435; 6,215,005 and 6,258,961 disclose the processes for separating the S (+)-enantiomer of clopidogrel.

U.S. Pat. No. 6,800,759 discloses a process for resolution of racemic clopidogrel and racemization of R (−) enantiomer.

A problem with the preparation of clopidogrel is the presence of a therapeutically inactive enantiomer, the R (−) enantiomer. The presence of the R (−) enantiomer results in contamination of the final product, and lowers the yield. The skilled artisan is aware of few racemization processes utilizing a base. However, there exists a need for an industrial process for recycling the R (−) enantiomer via racemization and resolving the desired enantiomers. This recycling of the R (−) enantiomer improves the overall yield of the product and makes this process cost effective.

SUMMARY OF THE INVENTION

In one aspect there is provided a process for preparing racemic clopidogrel or salts thereof. The process includes obtaining a solution of R(−) clopidogrel in one or more solvents; contacting the solution with a powered anhydrous base; and recovering the racemic clopidogrel from the solution by removal of the solvent.

Removing the solvent may include one or more of distillation, distillation under vacuum, filtration, filtration under vacuum, evaporation, decantation and centrifugation.

In another aspect there is provided a process for the preparation of S (+) clopidogrel or salts thereof. The process includes racemizing R(−) clopidogrel with a powered anhydrous base in one or more solvents; contacting the solution; recovering racemic clopidogrel; and resolving the racemic clopidogrel using a chiral auxiliary to obtain the S (+) clopidogrel.

R(−) clopidogrel formed during the reaction can be recycled. The mother liquor obtained from the reaction containing R (−) clopidogrel can again be reacted with a powdered anhydrous base in a solvent to get the racemic clopidogrel base.

The racemic clopidogrel base can again be resolved to obtain optically pure dextrorotatory isomer of the clopidogrel or can be recycled into next batch for the preparation of S (+) clopidogrel.

The S (+) clopidogrel can be converted to its salts.

The process may produce the S (+) clopidogrel or salts thereof having purity more than 99% when measured by HPLC. In particular, it may produce the pure S (+) clopidogrel or salts thereof having purity more than 99.9% when measured by HPLC.

In another aspect there is provided a pharmaceutical composition that includes a therapeutically effective amount of pure S (+) clopidogrel or a salt thereof having purity more than 99.9% by HPLC; and one or more pharmaceutically acceptable carriers, excipient or diluents.

The details of one or more embodiments of the inventions are set forth in the description below. Other features, objects and advantages of the inventions will be apparent from the description and claims.

DETAILED DESCRIPTION OF THE INVENTION

The inventors have developed a process for preparing racemic clopidogrel by racemizing R(−) clopidogrel. The process includes the step of reacting R(−) clopidogrel with a powered anhydrous base in one or more solvents.

The inventors while working on the racemization process have come up with a simple improvement of using the anhydrous base in a powdered form, which allows complete racemization of the R (−) enantiomer and thus contributes to better yield and purity.

Non-limiting examples of the base may include one or more of sodium carbonate, potassium carbonate, lithium hydroxide, sodium t-butoxide, potassium t-butoxide, diisopropylamide, sodium hydride, potassium hydride, sodium methoxide and potassium methoxide, and the like.

The racemization may be carried out in one or more solvents. The term 'solvents' includes any solvent or solvent mixture in which R (−) clopidogrel can be solubilized, including, for example, alcohols, ketones, esters, ethers, acetic acid and mixtures thereof.

A suitable alcohol includes one or more of methanol, ethanol and isopropanol. Examples of ketones include acetone and methyl isobutyl ketone. Examples of esters include ethyl acetate and methyl acetate. Examples of ethers include 2-methoxyethanol, tetrahydrofuran and isopropyl ether.

The solution of R (−) clopidogrel in a solvent can be obtained by dissolving, slurrying, stirring or a combination thereof or it may be obtained from a mother liquor of a reaction in which S (+) clopidogrel is formed and can be used as such.

The racemization reaction may be carried out at a temperature from about 0° C. to about 45° C.

The racemic clopidogrel may have specific optical rotation from (−)1° to (+)1°.

The racemic clopidogrel so obtained may be used as a starting material for the synthesis of clopidogrel and its enantiomers and salts thereof.

The inventors also have developed a process for the preparation of S (+) clopidogrel or a salt thereof. The process includes the steps of:

1. a) preparing a salt of racemic clopidogrel with a chiral auxiliary;
1. b) separating S (+) clopidogrel and R (−) clopidogrel from reaction mixture;
1. c) racemizing the R (−) clopidogrel obtained in step b) with a powdered anhydrous base in a solvent to get racemic clopidogrel;
1. d) repeating steps a) to step c) with the racemic clopidogrel obtained in step c); and
1. e) optionally, converting the S (+) clopidogrel obtained in step b) to pharmaceutically acceptable salts thereof.

The S (+) clopidogrel or salts thereof has a purity of more than 99.0%. More particularly, the purity of S (+) clopidogrel or salts thereof is more than 99.5%, for example more than 99.9%. The salts of clopidogrel may include bisulfate, hydrochloride, hydrobromide and other pharmaceutically acceptable salts.

The term 'Recycled' used herein means isolation of salt of R (−) clopidogrel with a chiral auxiliary from mother liquor and its use for the preparation of S (+) Clopidogrel or a salt thereof.

The R (−) enantiomer may be obtained by any of the processes known in the art. The R (−) clopidogrel may be obtained from a mother liquor of a reaction in which S (+) clopidogrel is formed and used as such. In particular, it may be obtained from the mother liquor of the reaction for preparation of S (+) clopidogrel or a salt thereof as described in U.S. Pat. No. 7,291,735. After isolation of the desired isomer salt S (+) of clopidogrel with a chiral auxiliary, the mother liquor enriched with R (−) enantiomers of clopidogrel with a chiral auxiliary may be concentrated and treated with sodium bicarbonate solution to get a free base of clopidogrel. The free base may be extracted into a suitable solvent and may be concentrated under reduced pressure to get a syrupy mass of the enriched R (−) clopidogrel. For recycling of the R (−) clopidogrel, the concentrated mass may be treated with a powdered anhydrous base to get the racemic clopidogrel. The racemic clopidogrel may be resolved using a chiral auxiliary to obtain optically pure dextrorotatory isomer of clopidogrel, which can be converted to its desired salts as per the process provided in U.S. Pat. No. 7,291,735, which is incorporated herein by reference. The recycling of the undesired enantiomer and its conversion into the desired enantiomer increases the overall yield of the process and hence makes this process more economical.

The term 'chiral auxiliary' includes the non-limiting examples of salts of clopidogrel with chiral acids such as L-tartaric acid, D-tartaric acid, di-p-anisoyl-D-tartaric acid, D-tartaric acid momoparachloro anilide, dibenzoyl-D-tartaric acid, Di-p-toluoyl-D-tartaric acid, Di-p-toluoyl-L-tartaric acid, D-lactic acid, D-malic acid, L(−)-camphor-10-sulphonic acid, S-hydratropic acid, (S)-2-methoxy phenyl acetic acid, (R)-2-methoxy-2-trifluoromethyl phenylacetic acid, D-mandelic acid, S(+)-1,1'-binaphthalene-2,2'-dihydrogen phosphate and mixtures thereof.

The term 'enriched' R(−) clopidogrel used herein may includes the presences of 5-30% of other isomers of clopidogrel with R(−) clopidogrel.

The organic solvent used for converting clopidogrel chiral auxiliary to a free base includes halogenated solvents for example, chloroform, methylene chloride, and the like.

The term 'Powdered' used herein includes the techniques known to a skilled artisan to reduce the particle size for example, grinding, pulverizing or milling. The particle size of the base may be reduced to 400 micron or below.

The moisture content of the powdered base may be 0.5% or less.

The inventors also have developed pharmaceutical compositions that contain the pure S (+) clopidogrel salt having purity more than 99.5% for example, more than 99.9%, in admixture with one or more pharmaceutically acceptable carriers, excipients or diluents.

The present invention is further illustrated by the following examples which are provided merely to be exemplary of the invention and do not limit the scope of the invention. Certain modifications and equivalents will be apparent to those skilled in the art and are intended to be included within the scope of the present invention.

Example 1

Preparation of α-bromo-2-(2-chlorophenyl)acetic acid methyl ester

α-Bromo-2-chlorophenyl acetic acid (350.0 gm) was dissolved in methanol (1.18 Liter) and concentrated sulphuric acid (53.20 gm) was added. The reaction mixture was refluxed for 4 hours. After completion of the reaction, the reaction mixture was distilled out to get a syrupy mass. To the residual mass, water (560 ml) was added and the product was extracted into chloroform (560 ml). The chloroform layer was separated and was treated with 10% aqueous sodium bicarbonate solution (1.12 Litre). The chloroform extract was finally washed with water and chloroform was distilled out to get a syrupy mass to get the titled compound.

Yield: 352.0 gm,
Purity: 95.85%.

Example 2

Step A: Preparation of Clopidogrel Camphor Sulfonate Salt

The methyl ester obtained in example 1 (352.0 gm) was dissolved in methanol (1.75 Liter) and sodium bicarbonate (264.65 gm) was added. To this reaction mixture, 4,5,6,7-tetrahydro thieno[3,2-c]pyridine hydrochloride (217.66 gm) was added and refluxed for 4 hours. After completion of the reaction, the methanol was distilled out to get a thick mass. To the thick mass so obtained, water (1.4 Liter) was added under stirring and it was extracted with chloroform (675 ml×2). The chloroform was distilled out to get a thick residual mass. The thick residual mass was dissolved in acetone (1.125 Liter) at 35-40° C. to get a clear solution and a solution of L(−)- camphor-10-sulphonic acid in acetone (170.69 gm dissolved in 635 ml of acetone) was added to it at 18-20° C. temperature. The mixture was further stirred at 10-12° C. for one hour followed by reflux for 4 hours. The mixture was cooled and the title compound was isolated. The mother liquor was not discarded and used for the recovery of clopidogrel.

Yield: 211.80 gm,
Specific rotation: +25.44°.

Step B: Preparation of S (+) Clopidogrel Base

The S (+) Clopidogrel camphor sulphonate salt (211.0 gm) was dissolved in chloroform (650 ml) and treated with 10% aqueous sodium bicarbonate solution (1.16 Liter). The reaction mixture was stirred for two hours. The chloroform layer was distilled out to get a syrupy mass of the title compound. S (+) clopidogrel was used in the next step without its isolation.

Example 3

Racemization of R (−) Clopidogrel Base

The mother liquor of example 2 Step A, was treated with 10% sodium bicarbonate solution in chloroform to get R (−) clopidogrel base (102 gm). The R (−) clopidogrel base (102 gm) was treated with potassium carbonate (anhydrous, powdered 43.84 gm) in methanol at 15-20° C. for 24 hrs. After completion of the reaction, the reaction mixture was filtered and the filtrate was subjected to distillation to recover methanol to get racemic clopidogrel base.

Assay: 95.7%
Specific angle of rotation: (+)0.42°

Example 4

Racemization of R (−) Clopidogrel Base

The enriched R (−) clopidogrel base (50 gm) was treated with potassium carbonate (anhydrous, powdered 21.5 gm) in methanol at 15-20° C. for 24 hrs. After completion of the reaction, the reaction mixture was filtered and the filtrate was subjected to distillation to recover methanol to get racemic clopidogrel base.

Assay: 96.3%
Specific angle of rotation: (−)0.22°

Example 5

Preparation of S (+) Clopidogrel Hydrochloride

S (+) Clopidogrel, 90 gm was dissolved in ethyl acetate (1.0 Liter) and the solution was concentrated at atmospheric pressure to half the original quantity. The reaction mixture was cooled to room temperature. To the residue, isopropanolic hydrochloric acid solution (26.0% w/v, 540.0 ml) was added. The reaction mixture was stirred at room temperature for two hours and the titled compound was isolated.

Yield: 78 gm
Purity by HPLC: 99.9%

Example 6

Preparation of S (+) Clopidogrel Bisulfate

S (+) clopidogrel, 90 gm was dissolved in ethyl acetate (1.0 Liter). It was stirred and sulfuric acid 30 gm was added at room temperature. After complete addition of sulfuric acid, the reaction mixture was heated at reflux for 1 hour. It was then cooled and further stirred at room temperature for 1 hour. The product so obtained was filtered under vacuum at 60-70° C. for 6-8 hours.

Yield: 80.0 gm
Purity by HPLC: 99.96%

While the present invention has been described in terms of its specific embodiments, certain modifications and equivalents will be apparent to those skilled in the art and are intended to be included within the scope of the present invention.

The invention claimed is:

1. A process for the preparation of racemic clopidogrel, the process comprising:
    a) obtaining a solution of R(−) clopidogrel in one or more solvents;
    b) contacting the solution with powdered anhydrous base having a particle size 400 micron or less; and
    c) recovering the racemic clopidogrel from the solution by removal of the solvent.

2. The process of claim 1, wherein the R(−) clopidogrel is obtained from a mother liquor of a reaction in which S (+) clopidogrel was formed and subsequently removed from the reaction mixture.

3. The process of claim 1, wherein the base is selected from the group consisting of sodium carbonate, potassium carbonate, and lithium hydroxide.

4. The process of claim 1, wherein the solvent comprises one or more alcohols, ketones, esters, ethers, acetic acid, or mixtures thereof.

5. The process of claim 4, wherein the alcohol comprises one or more of methanol, ethanol and isopropanol.

6. The process of claim 4, wherein the ketone comprises one or both of acetone and methyl isobutyl ketone.

7. The process of claim 4, wherein the ester comprises one or both of ethyl acetate and methyl acetate.

8. The process of claim 4, wherein the ether comprises one or more of 2-methoxyethanol, tetrahydrofuran and isopropyl ether.

9. A process for the preparation of S (+) clopidogrel or salts thereof, the process comprising the steps of:
    a) preparing a salt of racemic clopidogrel with a chiral auxiliary;
    b) separating the S (+) clopidogrel and R (−) clopidogrel isomers;
    c) racemizing the R (−) clopidogrel obtained in step b) with a powdered anhydrous base having a particle size of 400 micron or less, in a solvent to get racemic clopidogrel;
    d) repeating steps a) to step c) with the racemic clopidogrel obtained in step c); and
    e) optionally, converting the S (+) clopidogrel obtained in step b) to pharmaceutically acceptable salts thereof.

10. The process of claim 9, wherein the chiral auxiliary comprises one or more of L-tartaric acid, D-tartaric acid, di-p-anisoyl-D-tartaric acid, D-tartaric acid momoparachloro anilide, dibenzoyl-D-tartaric acid, Di-p-toluoyl-D-tartaric acid, Di-p-toluoyl-L-tartaric acid, D-lactic acid, D-malic acid, L(−)-camphor-10-sulphonic acid, S-hydratropic acid, (S)-2-methoxy phenyl acetic acid, (R)-2-methoxy-2-trifluoromethyl phenylacetic acid, D-mandelic acid, S(+)-1,1'-binaphthalene-2,2'-dihydrogen phosphate and mixtures thereof.

* * * * *